United States Patent [19]
Laas et al.

[11] Patent Number: 5,237,058
[45] Date of Patent: Aug. 17, 1993

[54] POLYISOCYANATES CONTAINING URETDIONE AND/OR ISOCYANURATE GROUPS, A PROCESS FOR THEIR PRODUCTION

[75] Inventors: Hans J. Laas, Cologne; Reinhard Halpaap, Odenthal-Gloebusch; Josef Pedain, Cologne, all of Fed. Rep. of Germany

[73] Assignee: Bayer Aktiengesellschaft, Leverkusen, Fed. Rep. of Germany

[21] Appl. No.: 774,687

[22] Filed: Oct. 11, 1991

[30] Foreign Application Priority Data

Oct. 19, 1990 [DE] Fed. Rep. of Germany ....... 4033288

[51] Int. Cl.$^5$ ............................................ C07D 229/00
[52] U.S. Cl. ..................................... 540/202; 528/45; 528/67; 528/73
[58] Field of Search ......................................... 540/202

[56] References Cited

U.S. PATENT DOCUMENTS

| | | | |
|---|---|---|---|
| 3,645,979 | 2/1972 | Liebsch et al. | 260/77.5 NC |
| 4,476,054 | 10/1984 | Disteldorf et al. | 260/239 A |
| 4,614,785 | 9/1986 | Richter et al. | 528/45 |
| 4,668,780 | 5/1987 | Disteldorf et al. | 540/202 |
| 4,994,541 | 2/1991 | Dell et al. | 528/51 |

FOREIGN PATENT DOCUMENTS

| | | |
|---|---|---|
| 1934763 | 1/1971 | Fed. Rep. of Germany . |
| 2502934 | 7/1976 | Fed. Rep. of Germany ...... 540/202 |
| 1244416 | 9/1971 | United Kingdom . |
| 1488631 | 10/1977 | United Kingdom . |
| 1153815 | 5/1989 | United Kingdom . |

*Primary Examiner*—Mukund J. Shah
*Assistant Examiner*—Y. N. Gupta
*Attorney, Agent, or Firm*—Joseph C. Gil; Thomas W. Roy

[57] ABSTRACT

The present invention relates to a process for the production of polyisocyanates containing uretdione and/or isocyanurate groups by
a) partially oligomerizing the isocyanate groups of organic diisocyanates to form uretdione and/or isocyanurate groups in the presence of catalysts containing trivalent phosphorus,
b) terminating the oligomerization reaction at the desired degree of oligomerization by converting the catalyst into a catalytically inactive oxidized form by the addition of an oxidizing agent and
c) subsequently removing unreacted diisocyanate by thin-layer distillation.

The present invention also relates to the polyisocyanates containing uretdione and/or isocyanurate groups obtained by this process.

Finally, the present invention also relates to the use of these polyisocyanates, optionally blocked with blocking agents for isocyanate groups, as the isocyanate component in polyurethane coating compositions.

10 Claims, No Drawings

POLYISOCYANATES CONTAINING URETDIONE AND/OR ISOCYANURATE GROUPS, A PROCESS FOR THEIR PRODUCTION

BACKGROUND OF THE INVENTION

1. Field of the Invention

The present invention relates to a new process for the production of polyisocyanates containing uretdione and/or isocyanurate groups by the partial dimerization and/or trimerization (generic term: oligomerization) of the isocyanate groups of organic diisocyanates using catalysts containing trivalent phosphorus and termination of the oligomerization reaction with deactivation of the catalyst by oxidation, to the polyisocyanates obtainable by this process and to their use in polyurethane coating compositions.

2. Description of the Prior Art

The oligomerization of organic diisocyanates using catalysts containing trivalent phosphorus, in particular tertiary phosphines or peralkylated phosphorous acid triamides, is known from a number of publications. Thus, according to DE-OS 1,670,667 or DE-OS 1,954,093, mixtures of aromatic and aliphatic diisocyanates are reacted to provide polyisocyanates containing the isocyanurate groups corresponding to the diisocyanates in the presence of tertiary phosphines. In addition, it is known from DE-OS 1,670,720, 1,934,763, 3,900,053 and U.S. Pat. No. 4,614,785 that the same catalysts also accelerate the dimerization of aliphatic diisocyanates with formation of uretdione structures. According to DE-OS 3,080,513, 3,227,779 and 3,437,635, pure dimers of aliphatic diisocyanates can be obtained by catalysis with peralkylated phosphorous acid triamides, optionally in the presence of H-acidic co-catalysts as described in DE-OS 3,437,635.

To obtain products having specifically reproducible properties, the oligomerization reaction has to be terminated exactly at a predetermined point.

In the processes according to DE-OS 3,030,513 and 3,227,779, the catalyst is distilled off together with excess unreacted diisocyanate at the desired degree of oligomerization. The disadvantage of this procedure is that uncontrolled secondary reactions can occur during distillation because of the high temperatures. In addition, the distillate which contains the active catalyst and, accordingly, has only limited stability in storage has to immediately be further processed.

In most of the known processes described above, these difficulties are overcome by terminating the oligomerization reaction at a certain degree of oligomerization by deactivation of the catalyst before the excess unreacted diisocyanate is separated from the resin by distillation. The catalyst is generally deactivated by the addition of a catalyst poison. The catalyst poisons proposed in the relevant prior publications are generally compounds which react with the catalysts with salt formation. These compounds include alkylating agents such as methyl iodide, dimethyl sulfate and toluene sulfonic acid methyl ester (DE-OS 1,670,667 and 1,670,720); acylating agents such as benzoyl chloride, acetyl chloride, acetanhydride, succinic anhydride and chloroformic acid ester (DE-OS 1,670,667, 1,670,720 and 1,934,763); and acids such as chloroacetic acid, trichloroacetic acid, trifluoroacetic acid, methane sulfonic acid, perfluorobutane sulfonic acid, phosphoric acid, acidic phosphoric acid esters, gaseous hydrogen chloride and compounds giving off hydrogen chloride, e.g., carbamic acid chlorides (DE-OS 1,670,667 and 3,437,635). In addition, phosphine catalysts can be deactivated with, for example, sulfonyl isocyanates (U.S. Pat. No. 4,614,785) and elemental sulfur (DE-OS 1,954,093).

However, when these catalyst poisons are used, numerous difficulties are encountered in practice. In the processes mentioned above, it is disclosed to deactivate the catalyst with an equimolar quantity of a stopper. However, since a certain quantity of catalyst is always consumed during the modification reaction, it is generally difficult to determine the exact quantity of catalyst poison required, i.e., the equimolar quantity. However, if too little of the stopper is used, part of the catalyst remains active which can lead during and after working up by distillation to the same problems which are encountered in the above-described processes which do not use catalyst poisons.

If these difficulties are overcome by using an excess quantity of stopper, the excess can enter the distillate during the removal of unreacted diisocyanate resulting in a distillate which is difficult or impossible to activate for recycling.

The reaction product formed from the catalyst and catalyst poison should have a higher boiling point than the monomeric diisocyanates used, should not decompose under the conditions used for working up by distillation and should therefore remain in the resin. This is generally the case when salt-forming catalyst poisons are used. However, the phosphine sulfides formed where phosphine catalysts are deactivated with elemental sulfur (DOS 1,954,093) are readily volatile under the conditions required for distillation, so that they accumulate as impurities in the distillate, particularly after several recycles.

In addition, some of the described catalyst poisons, for example, the sulfonic isocyanates according to U.S. Pat. No. 4,614,785, have an adverse effect on the color quality of the polyisocyanates formed.

Accordingly, it is an object of the present invention to provide a new process for the oligomerization of diisocyanates using known dimerization and/or trimerization catalysts which are not attended by any of the previously discussed difficulties of the prior art. It is an additional object of the present invention to deactivate the catalyst in such a way that, after the removal of excess monomeric diisocyanates by distillation complete stability of the polyisocyanate and distillate in storage would be obtained. It is a further object of the present invention to provide a resin which retains its reactivity to NCO-reactive groups and a distillate which is free from impurities and, thus, suitable for recycling. It is a final object of the present invention to provide to deactivate the catalyst without causing discoloration or cloudiness of the end product.

Surprisingly, this objects may be achieved in accordance with the process of the present invention which is described in detail hereinafter. The process according to the invention is based on the principle of converting the catalysts containing trivalent phosphorus, in particular tertiary phosphines, into pentavalent, catalytically inactive derivatives, in particular into the corresponding phosphine oxides, by treatment with suitable oxidizing agents.

SUMMARY OF THE INVENTION

The present invention relates to a process for the production of polyisocyanates containing uretdione and/or isocyanurate groups by
a) partially oligomerizing the isocyanate groups of organic diisocyanates to form uretdione and/or isocyanurate groups in the presence of catalysts containing trivalent phosphorus,
b) terminating the oligomerization reaction at the desired degree of oligomerization by converting the catalyst into a catalytically inactive oxidized form by the addition of an oxidizing agent and
c) subsequently removing unreacted diisocyanate by thin-layer distillation.

The present invention also relates to the polyisocyanates containing uretdione and/or isocyanurate groups obtained by this process.

Finally, the present invention also relates to the use of these polyisocyanates, optionally blocked with blocking agents for isocyanate groups, as the isocyanate component in polyurethane coating compositions.

DETAILED DESCRIPTION OF THE INVENTION

Starting materials for the process according to the invention include organic diisocyanates such as aliphatic, cycloaliphatic, araliphatic or aromatic diisocyanates having a molecular weight of 140 to 400 and mixtures of these diisocyanates.

Examples of such starting materials include 1,4-diisocyanatobutane, 1,6-diisocyanatohexane, 1,5-diisocyanato-2, 2-dimethyl pentane, 2,2,4- or 2,4,4-trimethyl-1,6-diisocyanatohexane, 1,10-diisocyanatodecane, 1,3- and 1,4-diisocyanatocyclohexane, 1-isocyanato-3,3,5-trimethyl-5-isocyanatomethyl cyclohexane (isophorone diisocyanate or IPDI), 1,3- and 1,4-xylylene diisocyanate, 4,4'-diisocyanatodicyclohexyl methane, 1,3- and 1,4-bis-(2-isocyanatoprop-2-yl)-benzene, 1-isocyanato-1-methyl-4(3)-isocyanatomethyl cyclohexane, 4-(4'-methyl-3'-isocyanatobenzyl)-cyclohexyl isocyanate, 2,4-and 2,6-diisocyanatotoluene, 2,4'- and 4,4'-diisocyanatodiphenyl methane, 1,5-diisocyanatonaphthalene and mixtures thereof.

Diisocyanates containing (cyclo)aliphatically bound isocyanate groups are preferably used as starting materials in the process according to the invention. 1,6-diisocyanatohexane (HDI) and isophorone diisocyanate (IPDI) are particularly preferred starting materials for the process according to the invention.

Suitable catalysts for the process according to the invention include organic compounds containing trivalent phosphorus, preferably tertiary organic phosphines, peralkylated phosphorous acid triamides and mixtures thereof as disclosed in U.S. Pat. No. 4,614,785 (herein incorporated by reference) at column 4, line 11 to column 5, line 5. Preferred catalysts for the process according to the invention are those which in the oxidized form have a higher boiling point than the monomeric diisocyanates used.

Accordingly, when 1,6-diisocyanatohexane and/or isophorone diisocyanate is used as the starting diisocyanate in the process according to the invention, tri-n-octyl phosphine is the particularly preferred catalyst.

The catalysts according to the invention are generally used in quantities of 0.01 to 5% by weight, preferably in quantities of 0.1 to 2% by weight, based on the quantity of starting diisocyanate used.

Organic compounds which contain at least one hydrogen atom attached to oxygen, nitrogen or sulfur and which have a pKa value of at least 6, as described in DE-OS 3 437 635, page 11, line 8 to page 16, line 6, (U.S. Pat. No. 4,929,724, herein incorporated by reference at column 3, line 56 to column 5, line 58) may optionally be used as co-catalysts in the process according to the invention.

Preferred co-catalysts are low molecular weight monohydric or polyhydric alcohols, more preferably those having a molecular weight of 32 to 200, and mixtures of these alcohols. Examples of suitable co-catalysts include methanol, ethanol, n-propanol, isopropanol, n-butanol, n-hexanol, 2-ethyl-1-hexanol, 1-methoxy-2-propanol, ethylene glycol, propylene glycol, the isomeric butanediols, hexanediols or octanediols, diethylene glycol, dipropylene glycol, 2-ethylhexane-1,3-diol, 2,2,4-trimethyl pentanediol, glycerol, trimethylol propane and mixtures of these alcohols.

The co-catalysts are used, if at all, in a positive quantity of up to 5% by weight, preferably 0.5 to 3% by weight, based on the starting isocyanate. The co-catalysts react with the starting diisocyanate to form urethane groups. These urethanes represent the actual co-catalysts. Accordingly, it is also possible to use separately prepared urethanes as co-catalysts instead of the alcohols mentioned by way of example.

In the process according to the invention, the catalyst is deactivated with a known oxidizing agent which converts the trivalent phosphorus compounds, preferably tertiary phosphines, into the corresponding pentavalent phosphorus compounds, preferably the corresponding phosphine oxides, as described for example in Houben-Weyl, Methoden der organischen Chemie, 4th Edition, Vol. E2, pages 41 to 48, Vol. IV/Id, pages 570 to 574, Vol. XII/1, pages 140 to 144 and Vol. XII/2, pages 109, 474. Preferably, the oxidizing agent is chosen such that its color does not adversely affect the color quality of the products according to the invention.

Suitable oxidizing agents include hydroperoxides such as tert. butyl hydroperoxide, cumene hydroxide and butanone peroxide; dialkyl and diacyl peroxides such as diethyl peroxide, di-tert. butyl peroxide, diamyl peroxide, dibenzoyl peroxide and dilauroyl peroxide; peroxycarboxylic acids such as peracetic acid, perbenzoic acid, m-chloroperbenzoic acid, and tert. butyl esters of these acids; hydrogen peroxide; oxygen; air; and mixtures of these oxidizing agents.

The oxidizing agents mentioned above, when they are present in solid form, liquid form or in their commercially available form as a solution, are generally added in such quantities that there is at least 1 mole and at most 3 moles "active" oxygen for every mole of catalyst used.

When oxygen or air is used to deactivate the catalyst, as is preferably the case, oxygen is passed through the reaction mixture in at least an equimolar quantity to the quantity of catalyst, but generally in several times the equimolar quantity. Alternatively, a volume of air containing this quantity of oxygen is passed through the reaction mixture. When the reaction is terminated in this way, it can be advantageous to add small quantities of a radical initiator, e.g., compounds such as $\alpha,\alpha'$-azoisobutyronitrile (AIBN) or the (hydro)peroxides mentioned above such as butanone peroxide. When a radical initiator is used, it is introduced before the oxygen or air in quantities of 50 to 500 ppm, based on the weight of the reaction mixture.

The process according to the invention is carried out in known manner as described for example in DE-OS 1,670,720, 1,954,093 or 3,437,635 (U.S. Pat. No. 4,929,724, herein incorporated by reference).

In general, the starting diisocyanate or mixture of starting diisocyanates is mixed with a catalyst which is suitable for the purposes of the invention at a temperature of −20° to 100° C., preferably 10° to 80° C., optionally in an inert gas atmosphere, and the oligomerization reaction takes place at a temperature within these ranges.

The previously mentioned co-catalysts may optionally be added to the reaction mixture before or during the oligomerization reaction. The oligomerization reaction is terminated after reaching the desired degree of oligomerization, which can be monitored by analytically determining the NCO content of the reaction mixture. In general, the oligomerization reaction is terminated after reaching a degree of oligomerization of 10 to 60%, preferably 10 to 50%. The "degree of oligomerization" is the percentage of isocyanate groups in the starting diisocyanate which react to form dimers and/or trimers and, optionally, urethane groups from a reaction with an NCO-reactive co-catalyst.

To terminate the oligomerization reaction, the previously mentioned solid or liquid oxidizing agents are added to the reaction mixture either in bulk or, optionally, in dissolved form, followed by heating for 15 to 120 minutes at a temperature of 10° to 100° C. Gaseous oxidizing agents (preferably air or oxygen) are passed through the reaction mixture heated to these temperatures.

After the reaction has been terminated in accordance with the invention, excess unreacted diisocyanate may be removed by known methods, such as thin-layer distillation, and reused. Long reaction times and high temperatures within the ranges mentioned generally promote the formation of trimers (isocyanurates); whereas, short reaction times and comparatively low temperatures within the ranges mentioned promote the formation of dimers (uretdiones).

The process according to the invention may optionally be carried out in the presence of solvents which are inert to isocyanate groups. Suitable solvents include hexane, toluene, xylene, chlorobenzene, ethyl acetate, butyl acetate, ethyl glycol acetate, propylene glycol monomethyl ether acetate, acetone, methyl isobutyl ketone, methylene chloride, N-methyl pyrrolidone and mixtures of such solvents.

The products obtained according to the invention from the preferred (cyclo)aliphatic diisocyanates may be solid or liquid at room temperature after they have been freed from excess monomeric starting diisocyanate. Cycloaliphatic diisocyanates, such as IPDI, generally result in solid end products, while liquid products are generally obtained from aliphatic diisocyanates such as HDI. The content of monomeric starting diisocyanate is generally below 1% by weight, preferably below 0.3% by weight.

The color-lightening effect of inorganic and organic peroxides on modified polyisocyanates which is known from DE-OS 3,900,053 (U.S. Pat. No. 4,994,541) and occurs as a secondary effect when the reaction is terminated by oxidation has proved to be particularly advantageous in the process according to the invention. Accordingly, the products obtained by the process according to the invention are less colored than analogous modified polyisocyanates produced using catalyst poisons according to the prior art.

When the particularly preferred starting diisocyanates, hexamethylene diisocyanate or isophorone diisocyanate, and the particularly preferred catalyst, tri-n-octyl phosphine (TOP), are used, oxidative termination of the reaction by the process according to the invention results in a reaction mixture in which the catalyst has been quantitatively converted into tri-n-octyl phosphine oxide (TOPO), as determined by gas chromatography.

The higher boiling point of the TOPO when compared with the boiling points of HDI and IPDI enables unreacted excess diisocyanate to be recovered in pure form, i.e., without contamination by deactivated catalyst, provided that distillation is carried out under suitable conditions.

According to gas chromatographic analysis and phosphorus determination by elemental analysis of the end products of the process according to the invention and the diisocyanates recovered, the phosphine oxide completely remains in the distillation residue, thus precluding accumulation in the distillate, even during repeated recycling.

The end products of the process according to the invention are completely stable in storage in regard to NCO content, viscosity and color quality. They are valuable starting materials for the production of polyurethanes, preferably one-component or two-component polyurethane coating compositions, by the polyisocyanate polyaddition process. When blocked with known blocking agents they are valuable starting materials for polyurethane stoving lacquers.

Preferred reactants for the polyisocyanates obtained according to the invention for production of polyurethane coating compositions are known and include polyhydroxy polyesters, polyethers and polyacrylates, polycarboxylic acids and, optionally, low molecular weight polyhydric alcohols. Polyamines, particularly in blocked form as polyketimines or oxazolidines, are also useful reactants for the polyisocyanates obtained according to the invention.

The quantitative ratios are generally selected to provide 0.8 to 3, preferably 0.9 to 1.1 hydroxy, amino and/or carboxyl groups for each optionally blocked isocyanate group.

Curing may be accelerated by using known catalysts, e.g., tertiary amines such as triethyl amine, pyridine, methyl pyridine, benzyl dimethyl amine, N,N-endoethylene piperazine, N-methyl piperidine, pentamethyl diethylenetriamine, N,N-dimethylaminocyclohexane and N,N'-dimethyl piperazine; and metal salts such as iron(III) chloride, zinc chloride, zinc-2-ethyl caproate, tin(II) ethyl caproate, dibutyl tin(IV) dilaurate and molybdenum glycolate.

When the polyisocyanates obtained according to the invention are used in stoving lacquers, their NCO groups are completely or partly blocked in known manner by reaction with a suitable blocking agent, preferably at elevated temperature, and optionally in the presence of one of the catalysts described above.

Suitable blocking agents include monophenols such as phenol and the cresols; tertiary alcohols such as tert. butanol and dimethyl phenyl carbinol; readily enolizable compounds such as acetoacetic ester and malonic acid derivatives; secondary aromatic amines such as N-methyl aniline and N-phenyl xylidine; imides such as succinimide; lactams such as ε-caprolactam and δ-valerolactam; oximes such as butanone oxime and cyclohexanone oxime; mercaptans such as methyl mercaptan and ethyl mercaptan; and triazoles such as 1H-1,2,4-triazole.

The coating composition may be produced by thoroughly mixing and homogenizing the optionally blocked polyisocyanate, polyfunctional reactants, catalyst and, optionally, known additives (such as pigments, fillers, dyes and flow control agents) with one another in a standard mixing unit, for example in a sand mill, either in the presence or absence of solvents and diluents.

Suitable solvents include known paint solvents such as ethyl acetate, butyl acetate, ethylene glycol monomethyl or monoethyl ether acetate, 1-methoxypropyl-2-acetate, 2-butanone, 4-methyl-2-pentanone, cyclohexanone, toluene, xylene, solvent naphtha and mixtures thereof. However, solvents such as N-methyl pyrrolidone or N-methyl caprolactam and plasticizers such as those based on phosphoric acid, sulfonic acid or phthalic acid esters, are also suitable.

The paints and coating compositions may be applied in solution, from the melt or in solid form to the article to be coated by known methods such as spread costing, roll coating, casting, spray coating, fluidized bed coating or electrostatic powder spraying.

The invention is illustrated by the following examples in which all parts and percentages are by weight, unless otherwise indicated.

EXAMPLES

Example 1

15 g of 2,2,4-trimethyl pentane-1,3-diol (TMPD) and 4.5 g of tri-n-octyl phosphine (TOP) were successively added at 50° C. to 1,500 g of HDI and subsequently heated to 60° C. After a reaction time of 5 h, the NCO content of the mixture was 41.2%. The reaction was terminated by adding 2.6 g of butanone peroxide (50% in dimethyl phthalate) and heating for 1 hour to 80° C. Thereafter and also after storage for 2 days, the NCO content of the crude product was 40.8%. After removal of the unreacted monomeric diisocyanate by thin-layer distillation (140° C./0.05 mbar), 485 g of a pale yellow product having an NCO content of 21.2%, a viscosity of 180 mPa.s (23° C.) and a residual monomeric HDI content of 0.3% were obtained. The content of uretdione groups (expressed as $C_2N_2O_2$, molecular weight 84) as determined by hot titration (3 h/180° C. in o-dichlorobenzene), was 15.3%. In addition, the IR spectrum showed the presence of isocyanurate groups (1689, 1465 cm$^{-1}$).

According to analysis, the distillate contained less than 1 ppm phosphorus.

Neither the resin nor the distillate showed any reduction in NCO content after storage for 8 weeks.

Example 2

1,000 g of HDI were reacted with 10 g of 2,2,4-trimethyl-1,3-pentanediol (TMPD) at 50° C. After the NCO content of the mixture had fallen to 48.9%, 3.0 g of tri-n-octyl phosphine (TOP) were added and the mixture was heated to 60° C. After 5 h and 30 minutes, the NCO content of the mixture was 42.5%. To terminate the reaction, 100 mg of α,α'-azo-isobutyronitrile (AIBN) were added, the mixture was heated to 80° C. and a stream of dry oxygen (approx. 15 l/h) was passed through the mixture for 1 h. After cooling to room temperature and after storage for 1 day, the NCO content was 42.5%. The excess quantity of unreacted monomeric diisocyanate was removed by thin-layer distillation at 130° C. under a pressure of 0.05 mbar to provide 246 g of a pale yellow product having an NCO content of 21.5%, a viscosity of 150 mPa.s (23° C.) and a monomeric HDI content of 0.3%. The content of uretdione groups (expressed as $C_2N_2O_2$, molecular weight 84) as determined by hot titration (3 h/180° C. in o-dichlorobenzene) was 17.2%.

According to elemental analysis, the distillate contained no phosphorus. Neither the resin nor the distillate showed any reduction in NCO content after storage for 4 weeks.

Example 3

10 g of TMPD and 3 g of TOP were successively added to 1,000 g of HDI at 50° C., followed by heating for 7 h at 60° C. The reaction mixture then had an NCO content of 40.6%. The oligomerization reaction was terminated by adding 5 ml of t-butyl hydroperoxide (3M in isooctane) and heating for 1 hour to 80° C. The NCO content of the crude product was 40.4%. The excess unreacted HDI was removed by thin-layer distillation at 130° C. under a pressure of 0.05 mbar to provide 303 g of a pale yellow product having an NCO content of 21.2%, a viscosity of 300 mPa.s (23° C.) and a residual content of monomeric HDI of 0.1%. The content of uretdione groups (expressed as $C_2N_2O_2$) as determined by hot titration (3 h/180° C. in o-dichlorobenzene), was 16.5%. According to analysis, the distillate contained less than 1 ppm phosphorus. Neither the resin nor the distillate showed any reduction in NCO content after storage for 4 weeks.

Example 4

1 g of TMPD and 0.3 g of TOP were added to 1,000 g of HDI at 50° C., followed by stirring for 6 h at 60° C. The reaction mixture then had an NCO content of 41.3%. 0.5 ml of a 2-molar solution of tert.-butyl hydroperoxide in isooctane was added and the mixture was heated for 1 h to 80° C. After cooling to room temperature and also after storage for 30 days, the NCO content of the mixture was 40.4%.

Example 5

2 g of TMPD and 0.6 g of TOP were added to 200 g of HDI at 50° C. After 3.5 h at 60° C., the NCO content of the mixture had fallen to 43.8%. After adding 0.35 g of butanone peroxide (50% in dimethyl phthalate) and heating for 1 hour to 80° C., the reaction mixture had an NCO content of 43.7% which remained constant during storage for 30 days at room temperature.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a polyisocyanate containing uretdione and/or isocyanurate groups which comprises
   a) partially oligomerizing the isocyanate groups of an organic diisocyanate to form uretdione and/or isocyanurate groups in the presence of a catalyst containing trivalent phosphorus, b) terminating the oligomerization reaction at the desired degree of oligomerization by converting the catalyst into a catalytically inactive oxidized form by the addition of an oxidizing agent comprising air, oxygen and/or an organic peroxide and c) subsequently removing unreacted diisocyanate by thin-layer distillation.

2. The process of claim 1 which comprises conducting step (a) in the presence of an organic compound which contains at least one hydrogen atom attached to oxygen, nitrogen or sulfur and has a pKa value of at least 6 as co-catalyst.

3. The process of claim 1 wherein said catalyst comprises an organic tertiary phosphine.

4. The process of claim 1 wherein said catalyst comprises tri-n-octyl phosphine.

5. The process of claim 1 wherein said organic diisocyanate comprises a (cyclo)aliphatic diisocyanate containing 6 to 15 carbon atoms.

6. The process of claim 1 wherein said organic diisocyanate comprises 1,6-diisocyanatohexane and/or 1-isocyanato-3,3,5-trimethyl-5-isocyanatomethyl cyclohexane.

7. A process for the production of a polyisocyanate containing uretdione and/or isocyanurate groups which comprises a) partially oligomerizing the isocyanate groups of an organic (cyclo)aliphatic diisocyanate containing 6 to 15 carbon atoms to form uretdione and/or isocyanurate groups in the presence of an organic tertiary phosphine catalyst and in the presence of an organic compound which contains at least one hydrogen atom attached to oxygen, nitrogen or sulfur and has a pKa value of at least 6 as co-catalyst, b) terminating the oligomerization reaction at the desired degree of oligomerization by converting the catalyst into a catalytically inactive oxidized form by the addition of an oxidizing agent which comprises air, oxygen or an organic peroxide and c) subsequently removing unreacted diisocyanate by thin-layer distillation 8. The process of claim 7 wherein said organic tertiary phosphine catalyst comprises tri-n-octyl phosphine.

9. The process of claim 7 wherein said organic diisocyanate comprises 1,6-diisocyanatohexane and/or 1-isocyanato-3,3,5-trimethyl-5-isocyanatomethyl cyclohexane.

10. The process of claim 8 wherein said organic diisocyanate comprises 1,6-diisocyanatohexane and/or 1-isocyanato-3,3,5-trimethyl-5-isocyanatomethyl cyclohexane.

* * * * *